(12) United States Patent
Roman et al.

(10) Patent No.: US 7,307,101 B2
(45) Date of Patent: Dec. 11, 2007

(54) USE OF 20-HETE SYNTHESIZING ENZYME INHIBITORS AS THERAPY FOR CEREBRAL VASCULAR DISEASE

(75) Inventors: Richard J. Roman, Brookfield, WI (US); David R. Harder, Waukesha, WI (US); Noriyuki Miyata, Tokyo (JP); Masakazu Sato, Kohnosu (JP); Kazuya Kameo, Kohnosu (JP); Shigeru Okuyama, Kitamoto (JP)

(73) Assignees: MCW Research Foundation, Inc., Milwaukee, WI (US); Taisho Pharmaceutical Co., Ltd., Tokyo (JP)

( * ) Notice: Subject to any disclaimer, the term of this patent is extended or adjusted under 35 U.S.C. 154(b) by 454 days.

(21) Appl. No.: 09/937,946

(22) PCT Filed: Sep. 6, 2001

(86) PCT No.: PCT/US01/27605

§ 371 (c)(1),
(2), (4) Date: Oct. 7, 2002

(87) PCT Pub. No.: WO02/36108

PCT Pub. Date: May 10, 2002

(65) Prior Publication Data

US 2005/0153871 A1 Jul. 14, 2005

Related U.S. Application Data

(60) Provisional application No. 60/245,638, filed on Nov. 3, 2000.

(51) Int. Cl.
*A01N 37/34* (2006.01)
*A61K 37/275* (2006.01)
*C12N 9/10* (2006.01)

(52) U.S. Cl. ..................... 514/523; 435/193
(58) Field of Classification Search ................ 435/189
See application file for complete search history.

(56) References Cited

FOREIGN PATENT DOCUMENTS

| WO | WO 99/43310 | * | 9/1999 |
|---|---|---|---|
| WO | WO9943310 | | 9/1999 |
| WO | WO 01/32164 | | 10/2001 |

OTHER PUBLICATIONS del Zoppo et al Clinical trials in acute stroke: why have they not been successful? Neurology. Sep 1998;51(3 Suppl 3):S59-61. Review.*
Fotherby et al Stroke, blood pressure and antihypertensive therapy. J Hum Hypertens. Oct. 1997;11(10):625-7. Review.*
Frisbee et al Contribution of cytochrome P-450 omega-hydroxylase to altered arteriolar reactivity with high-salt diet and hypertension. Am J Physiol Heart Circ Physiol. May 2000;278(5):H1517-26.*
Kalaria et al Vascular endothelial growth factor in Alzheimer's disease and experimental cerebral ischemia. Brain Res Mol Brain Res. Nov. 12, 1998;62(1):101-5.*
Schmidt et al Vascular risk factors in dementia. J Neurol. Feb. 2000;247(2):81-7. Review.*
Su et al Inhibition of renal arachidonic acid omega-hydroxylase activity with ABT reduces blood pressure in the SHR. Am J Physiol. Aug 1998;275(2 Pt 2):R426-38.*
Zhang et al Vascular endothelial growth factor and angiopoietins in focal cerebral ischemia. Trends Cardiovasc Med. Feb. 2002;12(2):62-6. Review.*
Hoagland et al., Inhibitors of 20-HETE formation promote salt-sensitive hypertension in rats. Hypertension. Oct. 2003;42(4):669-73. Epub Jul. 21, 2003.*
Lasker et al., Formation of 20-hydroxyeicosatetraenoic acid, a vasoactive and natriuretic eicosanoid, in human kidney. Role of Cyp4F2 and Cyp4A11. J Biol Chem. Feb. 11, 2000;275(6):4118-26.*
Alonso-Galicia, M. et al., "Inhibition of 20-HETE Production Contributes to the Vascular Responses to Nitric Oxide," *Hypertension* 29:320-325 (1997).
Alonso-Galicia, M., et al., "Contribution of 20-HETE to Vasodilator Actions of Nitric Oxide in the Cerebral Microcirculation," *Stroke* 30:2727-2734 (1999).
Alonso-Galicia, M., et al., "20-HETE agonists and antagonists in the renal circulation," *Am. J. Physiol.* 277:F790-F796 (1999).
Amet, Y., et al., "Cytochrome P450 4A and 2E1 Expression in Human Kidney Microsomes," *Biochemical Pharmacology* 53:765-771 (1997).
Amet, Y., et al., "Noninvolvement of CYP2E1 in the (ω-1)-hydroxylation of Fatty Acids in Rat Kidney Microsomes," *Biochemical Pharmacology* 54:947-952 (1997).
Amet, Y., et al., "P-450-Dependent Metabolism of Lauric Acid in Alcoholic Liver Disease: Comparison Between Rat Liver and Kidney Microsomes," *Alcoholism: Clinical and Experimental Research* 22:455-462 (1998).
Bednar, M.M., et al., "1 6(R)-Hydroxy-5,8,11,14-eicosatetraenoic Acid, a New Arachidonate Metabolite in Human Polymorphonuclear Leukocytes," *Biochemical Pharmacology* 60:447-455 (2000).
Christmas, P., et al., "Alternative Splicing Determines the Function of CYP4F3 by Switching Substrate Specificity," *Journal of Biological Chemistry* 276:38166-38172 (2001).
Clozel, M. et al., "BQ-123, A Peptidic Endothelin $ET_A$ Receptor Antagonist, Prevents the Early Cerebral Vasospasm Following Subarachnoid Hemorrhage After Intracisternal But Not Intravenous Injection," *Life Sciences* 52:825-834 (1993).

(Continued)

*Primary Examiner*—Sheridan Swope
(74) *Attorney, Agent, or Firm*—Quarles & Brady LLP

(57) ABSTRACT

A method for treating cerebral vascular diseases in a human or non-human animal is disclosed. The method involves inhibiting 20-HETE synthesizing enzyme activity sufficiently to increase or prevent a decrease in cerebral blood flow in the human or non-human animal.

5 Claims, 11 Drawing Sheets

OTHER PUBLICATIONS

Croft, K., et al., "Angiotensin II releases 20-HETE from rat renal microvessels," *Am. J. Physiol. Renal Physiol.* 279:F544-F551 (2000).

Dahly, A.J., et al., "Chronic Anti-TGF-β Therapy Improves Blood Pressure and Renal Function in Dahl S Rats," *FASEB J.* 14:A133 (2000).

Dahly, A.J., et al. "Chronic Anti-TGF-β Ab Therapy Reduces Proteinuria and Renal Injury in Hypertensive Rats," *American Society of Hephrology Renal Week* 1 1:332A (2000).

Gebremedhin, D., et al., "Cat cerebral arterial smooth muscle cells express cytochrome P450 4A2 enzyme and produce the vasoconstrictor 20-HETE which enhances L-type $Ca^{2+}$current," *Journal of Physiology* 507.3:771-781 (1998).

Gebremedhin, D., et al., "Production of 20-HETE and Its Role in Autoregulation of Cerebral Blood Flow," *Circulation Research* 87:60-65 (2000).

Harder, D.R., et al., "Formation and action of a *P*-450 4A metabolite of arachidonic acid in cat cerebral microvessels," *American Physiological Society* 266:H2098-H2107 (1994).

Juvela S., "Plasma endothelin concentrations after aneurysmal subarchnoid hemorrhage," *J. Neurosurg.* 92:390-400 (2000).

Oyekan, A., et al., "Renal oxygenases: differential contribution to vasoconstriction induced by ET-1 and ANG II," *American Physiological Society* 273:R293-R300 (1997).

Powell, P.K., et al., "Metabolism of Arachidonic Acid to 20-Hydroxy-5,8,11,14-eicosatetraenoic Acid by P450 Enzymes in Human Liver:Involvement of CYP4F2 and CYP4A11," *Journal of Pharmacology and Experimental Therapeutics* 285:1327-1336 (1998).

Rosolowsky, M., "Metabolism of arachidonic acid by canine polymorphonuclear leukocytes synthesis of lipoxygenase and omega-oxidized metabolites," *Biochimica et Biophysica Acta* 1300:143-150 (1996).

Seifert, V., et al., "Endothelin concentrations in patients with aneurysmal subarachnoid hemorrhage," *J. Neurosurg.* 82:55-62 (1995).

Wang, M., et al., "Contribution of cytochrome *P*-450 4A1 and 4A2 to vascular 20-hydroxyeicosatetraenoic acid synthesis in rat kidneys," *American Physiological Society* 276L:F246-F253 (1999).

Wang, M., et al., "Cytochrome P450-Derived Arachidonic Acid Metabolism in the Rat Kidney:Characterization of Selective Inhibitors," *The Journal of Pharmacology and Experimental Therapeutics* 284:966-973 (1998).

Zou, A., et al., "Effects of 17-Octadecynoic Acid, a Suicide-Substrate Inhibitor of Cytochrome P450 Fatty Acid ω-Hydroxylase, on Renal Function in Rats," *The Journal of Pharmacology and Experimental Therapeutics* 268:474-481 (1994).

Lange, et al., 20-Hydroxyeicosatetraenoic acid-induced vasoconstriction and inhibition of potassium current in cerebral vascular smooth muscle is dependent on activation of protein kinase C. J Biol Chem. Oct. 24, 1997;272(43):27345-52.

Zou, et al., Inhibition of renal vascular 20-HETE production impairs autoregulation of renal blood flow. Am J Physiol. Feb. 1994;266(No. 2 Pt 2):F275-82.

Miyata, et al., HET0006, a potent and selective inhibitor of 20-HETE synthesizing enzyme. Br J Pharmacol. Jun. 2001;133(3):325-9.

\* cited by examiner

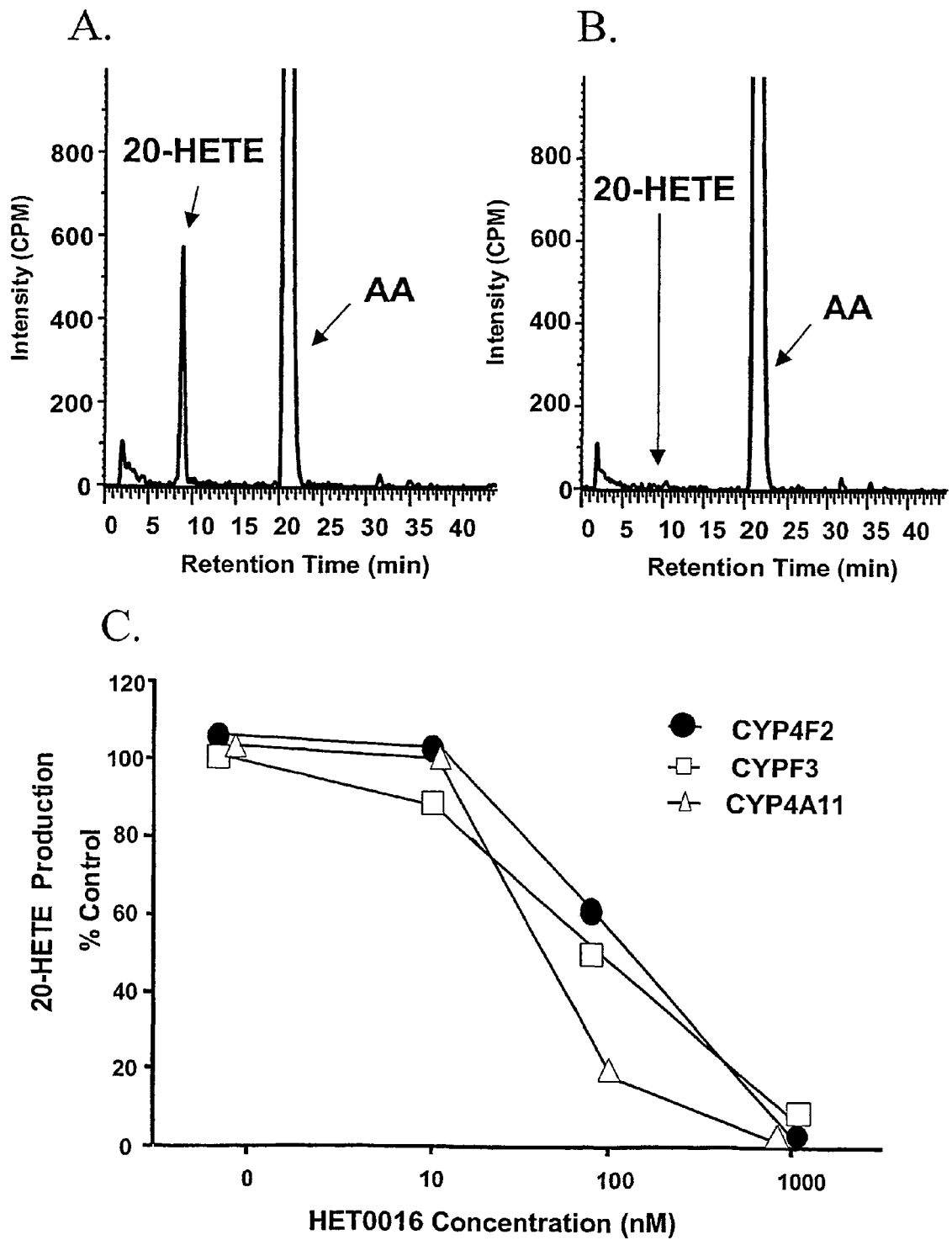

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
cagtgcagag acgctcatgg t                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 2
cagugcagag acgcucaugg u                                              21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gctaaataca gagaaaccca tggt                                           24

<210> SEQ ID NO 4
<211> LENGTH: 24
<212> TYPE: RNA
<213> ORGANISM: Artificial Sequence
<220> FEATURE:

-continued

```
<223> OTHER INFORMATION: Description of Artificial Sequence:
      oligonucleotide

<400> SEQUENCE: 4
gcuaaauaca gagaaaccca uggu                                              24
```

USE OF 20-HETE SYNTHESIZING ENZYME INHIBITORS AS THERAPY FOR CEREBRAL VASCULAR DISEASE

CROSS-REFERENCE TO RELATED APPLICATIONS

This application is a filing under 35 USC 371 of PCT/US01/27605, filed Sep. 6, 2001, and claims the benefit of U.S. provisional application Ser. No. 60/245,638, filed on Nov. 3, 2000.

STATEMENT REGARDING FEDERALLY SPONSORED RESEARCH OR DEVELOPMENT

This invention was made with United States government support awarded by the following agency: NIH Grant Nos. HL-59996 and HL-36279. The United States has certain rights in this invention.

BACKGROUND OF THE INVENTION

Reduced cerebral blood flow can cause a range of problems from light headaches to severe brain damage and death. There are many situations that can lead to reduced cerebral blood flow. Examples of such situations include hemorrhagic stroke, brain injuries, occlusive stroke, cerebral vasospasm and hypotension.

Subarachnoid hemorrhage (SAH) accounts for 5-10% of all strokes. The incidence is 2-20 events per 100,000 population per year with a case fatality rate of 20-60%. Ingall, T et al., *Stroke* 31: 1054-1061 (2000); *Stroke* 31: 1843-1850 (2000). SAH occurs most commonly after rupture of cerebral aneurysms or head trauma leading to subarachnoid bleeding and clot formation. After the bleeding, cerebral blood flow initially falls due to an elevated cerebrospinal fluid pressure that reduces effective perfusion pressure combined with the release of vasoactive agents from the blood that increases cerebral vascular tone. This initial phase of injury following SAH is associated with a high mortality (30-50%). Later cerebrovasospasm (CVS) develops with a delayed onset (2-3 days in rats, 5-7 days in human beings). The mortality associated with this delayed CVS is even more devastating and approaches 70%. Weir, B., *Br. J. Neurosurg* 9: 375-390 (1995). Very little is known about the factors that are released by blood and reduce cerebral blood flow in the initial phase after SAH. Even less is known about what mediates delayed CVS. Previous studies have indicated that the delayed CVS following SAH is associated with activation of protein kinase C (PKC), diminished activity of $K^+$ channels and depolarization of vascular smooth muscle (VSM) cells. Depolarization of cerebral VSM cells increases influx of calcium which potentiates the vasoconstrictor response to endothelin (ET), thromboxane, serotonin and other vasoconstrictors produced by clotting blood and diminishes the responsiveness of cerebral vessels to endogenously formed vasodilators such as nitric oxide (NO). The impaired response to NO has been postulated to be due to the binding of NO to free hemoglobin after hemolysis of erythrocytes, Edwards, D. H. et al., *J. Neurosurg.* 76: 830-837 (1992), or increased degradation of NO by superoxide formed by oxidation of hemoglobin. Misra, H. P. et al., *J. Biol. Chem.* 247: 6960-6962 (1972); Winterbourn C C et al., *Biochem. J.* 155: 493-502 (1976). Moreover, there is evidence that the activity of one of the second messengers of NO, soluble guanylyl cyclase, is reduced following SAH. Faraci, F. M. and Sobey, G. C., *Brain Res.* 821: 368-373 (1999); Sehba, F. A. et al., *Stroke* 30: 1955-1961 (1999).

Other studies have explored the role of upregulation of vasoconstrictor pathways in mediating CVS following SAH. ET levels increase after SAH. The initial fall in cerebral blood flow observed two hours after induction of SAH in rats is attenuated by inhibitors of the synthesis of ET and by ET receptor blockers. Clozel, M. and Watanabe, H., *Life Sci.* 52: 825-834 (1993). Enhanced fatty acid turnover and increased formation of vasoconstrictor metabolites of arachidonic acid (AA) have also been observed following SAH. Juvela S, *J. Neurosurg.* 92: 390-400 (2000); Seifert, V. et al., *J. Neurosurg.* 82: 55-62 (1995). Recent studies have indicated that 20-hydroxyeicosetetraenoic acid (20-HETE) is a metabolite of AA produced in the cerebral circulation. However, the role of 20-HETE in the pathogenesis of CVS following SAH is unknown. 20-HETE is produced by enzymes of the cytochrome P450 (CYP) 4A family that are expressed in VSM cells in cerebral arteries. Harder, D. R. et al., *Am J Physiol Heart Circ Physiol.* 266: H2098-H2107 (1994); Gebremendin, D. et al., *Circ Res.* 87: 60-65, 2000. The CYP4A family members for 20-HETE formation include CYP4A1, 2, 3 and 8 in rats, CYP4A10, 12 and 14 in mice, and CYP4A11 in human. Enzymes of the CYP4F family are also involved in 20-HETE production. The CYP4F family members for 20-HETE formation include CYP4F1, 4, 5 and 6 in rats, and CYP4F2 and 3 in human. CYP4F2 has been shown to produce 20-HETE when incubated with AA. Powell, P. K. et al., *J Pharmacol Exp Therap* 285: 1327-1336, 1998. CYP4F3 has been shown to be expressed in polymorphonuclear white blood cells that produce 20-HETE. Bednar, M. M. et al., *Biochem Pharmacol* 60: 447-455, 2000; Rosolowsky, M. et al., *Biochem Biophys Acta* 1300: 143-150, 1996.

20-HETE is a potent constrictor of cerebral arteries ($EC_{50}<10$ nM). 20-HETE activates PKC and depolarizes VSM cells by inhibiting the large conductance $K_{Ca}$ channel. 20-HETE also increases $Ca^{2+}$ influx via L-type $Ca^{2+}$ channels in the cerebral vasculature, Harder, D. R. et al., *Am J Physiol Heart Circ Physiol.* 266: H2098-H2107 (1994); Gebremedhin, D. et al., *J. Physiol (Lond).* 507 (Pt 3): 771-781 (1998), and plays a critical role in the mechanism underlying the autoregulation of cerebral blood flow in rats. Alonso-Galicia, M. et al., *Stroke* 30: 2727-2734 (1999); Gebremedhin, D. et al., *Circ. Res.* 87: 60-65 (2000). Vasoconstrictor peptides like angiotensin II and ET stimulate the formation of 20-HETE. Oyekan, A. et al., *Am J Physiol Regulatory Integrative Comp Physiol.* 273: R293-R300 (1997); Croft, K. D. et al., *Am. J. Physiol Renal Physiol.* 279: F544-F551 (2000). The vasodilator NO inhibits the formation of 20-HETE. Alonso-Galicia, M. et al., *Stroke* 30: 2727-2734 (1999). Activated polymorphonuclear leukocytes (PMN) and cerebral arteries avidly produce 20-HETE. Harder, D. R. et al., *Am J Physiol Heart Circ Physiol.* 266: H2098-H2107 (1994); Gebremedhin, D. et al., *J. Physiol (Lond).* 507 (Pt 3): 771-781 (1998); Alonso-Galicia M. et al., *Stroke* 30: 2727-2734 (1999); Gebremedhin, D. et al., *Circ. Res.* 87: 60-65 (2000); Bednar, M. M. et al., *Biochem. Pharmacol.* 60: 447-455 (2000); Rosolowsky, M. et al., *Biochem Biophys Acta* 1300: 143-150, 1996; Lange, A. et al., *J. Biol. Chem.* 272: 27345-27352 (1997). However, it is not known whether treating an animal with a 20-HETE synthesizing enzyme inhibitor will prevent the initial fall in cerebral blood flow associated with SAH (hemorrhagic stroke) or the delayed CVS and cerebral ischemia. Moreover, drugs that are currently available for inhibiting the formation of 20-HETE have serious limitations that greatly restrict their potential as therapeutic agents. For example, although 17-ODYA inhibits the synthesis of 20-HETE, it is not a specific inhibitor because it is equally effective at blocking the formation of EETs. Zou, A. P. et al., *J Pharmacol Exp Therap* 268: 474-481, 1994. EETs are potent vasodilators formed in the brain. Blockade of the synthesis of EETs may oppose any beneficial effects associated with blockade of the formation of 20-HETE. Alkayed, N. J. et al., *Am J Physiol Heart Circ Physiol* 271: H1541-H1546, 1996; Gebremendhin, D. et al., *Am J Physiol Heart Circ Physiol* 263: H519-H525, 1992. 17-Octadecynoic acid (17-ODYA) also binds to plasma proteins and does not cross the blood brain barrier when given systemically. DDMS is a more specific inhibitor of the formation of 20-HETE. Alonso-Galicia, M. et al., *Hypertension* 29:320-325, 1997; Wang, M. H. et al., *J Pharin Exp Therap* 284:966-973, 1998. However, it too binds to plasma proteins and does not cross the blood-brain barrier when given systemically.

The effects of intracerebroventricular injection of DDMS on cerebral blood flow has been examined in previous studies. DDMS has no effect on baseline cerebral blood flow. However, it blocks autoregulation of cerebral blood flow, i.e., constriction of cerebral vessels associated with elevations in cerebral blood flow. Gebremendin, D. et al., *Circ Res.* 87:60-65, 2000. DDMS has also been reported to prevent the rise in cerebral blood flow produced by the NO donor, DEA NONOate. Alonso-Galicia, M. et al., *Stroke* 30:2727-2734, 1999. However, there is no in vivo information available as to whether DDMS or 17-ODYA have beneficial effects in preventing or reversing a fall in cerebral blood flow such as that associated with SAH or stroke and other cerebral vascular diseases.

BRIEF SUMMARY OF THE INVENTION

In one embodiment, the present invention is a method for treating a cerebral vascular disease in a human or non-human animal by reducing 20-HETE synthesizing enzyme activity in the human or non-human animal sufficiently to increase cerebral blood flow or to prevent the fall in cerebral blood flow associated with various disease states. The term "cerebral vascular disease" means a condition triggered by a decrease in cerebral blood flow.

Reducing 20-HETE synthesizing enzyme activity can be achieved by using a 20-HETE synthesizing enzyme inhibitor. For the purpose of this invention, an inhibitor of 20-HETE synthesizing enzyme can be a chemical compound or an antibody to 20-HETE synthesizing enzyme. Reducing 20-HETE synthesizing enzyme activity can also be achieved by lowering the level of 20-HETE synthesizing enzyme such as treating the animal with an anti-sense oligonucleotide that blocks the translation of the mRNAs encoding for the CYP4A or CYP4F enzymes that produce 20 HETE.

BRIEF DESCRIPTION OF THE SEVERAL VIEWS OF THE DRAWINGS

FIG. 11 shows chromatograms of 20-HETE formation catalyzed by CYP4F3 in the presence (panel B) or absence (panel A) of HET0016 and the effect of HET0016 on 20-HETE formation catalyzed by CYP4A11, CYP4F2 and CYP4F3 (panel C).

DETAILED DESCRIPTION OF THE INVENTION

In general, the present invention provides a method for treating cerebral vascular diseases by reducing 20-HETE synthesizing enzyme activity sufficiently to increase cerebral blood flow or to prevent the fall in cerebral blood flow associated with various disease states. The term "cerebral vascular disease" means a condition triggered by a decrease in cerebral blood flow. The term "20-HETE synthesizing enzyme" includes enzymes of CYP4A and CYP4F families. In addition to CYP4A11 and CYP4F2, human enzyme CYP4F3 has recently been shown to produce 20-HETE. Chrismas P et al, Alternative splicing determines the function of CYP4F3 by switching substrate specificity, *J. Biol. Chem.* (2001). The term "treating" or "therapy" means preventing the development of a disease, reducing the severity of a disease at the onset of the disease, reducing the severity of a disease after the development of the disease, or making the symptoms of a disease disappear.

Figure 1:
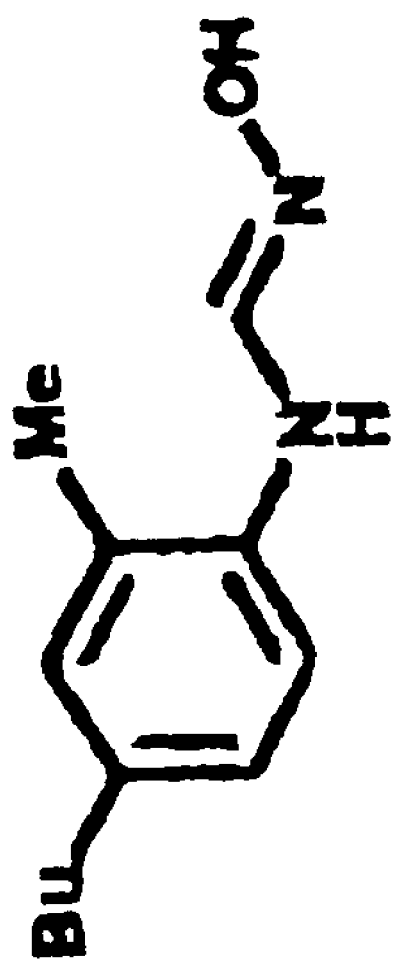
FIG. 1 shows the structure of N-hydroxy-N'-(4-butyl-2-methylphenyl)-formamidine (HET0016).

20-HETE is a blood vessel constrictor. In the examples described below, treating animals with a 20-HETE synthesizing enzyme inhibitor has been shown to lower 20-HETE levels in the animals and improve cerebral blood flow in those animals that suffer from cerebral vascular diseases. The therapeutic effect of a 20-HETE synthesizing enzyme inhibitor on cerebral vascular diseases was first tested in a hemorrhagic stroke model: SAH. In this model, the induction of SAH caused an increase in 20-HETE level. The increase of 20-HETE level following SAH or any hemorrhage in the brain is likely caused by activation of white blood cells during the clotting reaction and stimulation of 20-HETE production in the wall of the cerebral arteries. 20-HETE levels may also be increased by migration of white blood cells into the hemorrhage site following SAH, ischemic injury to brain following occlusive stroke, or inflammation or traumatic injury to the brain. The 20-HETE synthesizing enzyme inhibitors HET0016 (FIG. 1 for structure; Miyata, N. et al., HET0016, a potent and selective inhibitor of 20-HETE synthesizing enzyme, *Br. J. Pharmacol.* 133: 325-329, 2001; a method for synthesizing HET0016 is disclosed in PCT application PCT/JP00/07694, publication number WO 01/32164) and 17-ODYA (purchased from Sigma Chemical Corp., St. Louis, Mo.) were shown to effectively lower 20-HETE levels in the CSF following SAH. Pretreatment of rats with HET0016 or 17-ODYA prevented the fall in cerebral blood flow following SAH. HET0016 was also found to reverse the fall in cerebral blood flow after SAH was already initiated and the detrimental effects of elevated 20-HETE levels on cerebral blood flow and vascular tone were already evident. The beneficial effect of a 20-HETE synthesizing enzyme inhibitor on cerebral vascular diseases was further tested using an occlusive stroke model. In this model, the occlusive stroke was caused by transit occlusion of the middle cerebral artery. Pretreating rats with a 20-HETE synthesizing enzyme inhibitor HET0016 was shown to significantly decrease the infarct volume following occlusion of the middle cerebral artery. In this case, the source of 20 HETE is probably the PMNs that have infiltrated into the ischemic infarct area.

The cerebral vascular diseases that 20-HETE synthesizing enzyme inhibitors can treat are not limited to the above examples. Both activated white blood cells and cerebral arteries avidly produce 20-HETE. It is expected that 20-HETE synthesizing enzyme inhibitors can be used to treat conditions resulting from a diminished cerebral blood flow. Besides hemorrhagic strokes and occlusive strokes, these conditions include but are not limited to migraine headaches, CVS, infections, conditions caused by traumatic head and brain injury, and chronic neurological diseases associated with reduced blood flow such as Alzheimer's disease, dementia, Parkinson's disease and Huntington disease in which the condition can be mitigated by improving cerebral perfusion.

In the examples described below, HET0016 has been shown to be a highly specific 20-HETE synthesizing enzyme inhibitor in that, when used at a concentration which inhibited 20-HETE synthesizing enzyme by 80% or more, very little inhibition of the synthesis of EETs or of the other CYP enzymes tested was observed. Others have shown that DDMS is also a fairly specific inhibitor of enzymes that produce 20-HETE. Other 20-HETE synthesizing enzyme inhibitors such as 17-ODYA, 1-ABT (available from Sigma Chemical Corp., St. Louis, Mo.) and miconazole (available from Sigma Chemical Corp., St. Louis, Mo.) are far less specific in that they either inhibit the synthesis of EETs at least as well as they inhibit 20-HETE synthesis or they also inhibit some other CYP enzymes significantly while inhibiting 20-HETE synthesizing enzymes. Any 20-HETE synthesizing enzyme inhibitor can be used to treat cerebral vascular diseases. However, inhibitors with higher specificity such as HET0016 will likely be more advantageous because they are more likely to have less side effects.

As shown in the example described below, HET0016 inhibits 20-HETE formation in rat renal microsomes and in dog PMNs in a dose-dependent manner and the $IC_{50}$ of HET0016 for inhibiting rat 20-HETE synthesizing enzyme is between about 10 nM and about 25 nM. HET0016 inhibited synthesis of 20-HETE in human renal microsomes in a dose-dependent manner with an $IC_{50}$ of 8.9 nM. When tested with recombinant CYP4A11, 4F2 and 4F3 isoforms, HET0016 inhibited synthesis of 20HETE in a dose-dependent manner with an $IC_{50}$ between 50 nM to 100 nM. The lowest dose of HET0016 tested for inhibition of 20-HETE synthesizing enzyme was 1.5 nM and at this concentration, the rat 20-HETE synthesizing enzymes were inhibited by about 20%. Generally, it is expected that a HET0016 plasma concentration from about 1 nM to about 1,000 nM will be effective in treating cerebral vascular diseases. The term "about" used in the specification and claims in association with a dose means the dose also covers small variations therefrom that retain the general functionality of the dose. When HET0016 was injected i.v. at a dose of 10 mg/kg body weight, the HET0016 plasma level one hour later was 2.8 µM. It is expected that i.v. injection of about 0.003 mg/kg body weight to about 10 mg/kg body weight will result in plasma concentrations of HET0016 ranging from about 1.0 nM to about 2.8 µM and therefore will be effective in treating cerebral vascular diseases.

Besides i.v. injection, HET0016 may also be administered orally and subcutaneously. The dose required to reach a plasma level of about 1 nM to about 1,000 nM when HET0016 is administered orally or subcutaneously can easily be determined using the same method of measuring plasma HET0016 level described in the example below in which HET0016 was administered intravenously. In addition, in the case of a hemorrhagic stroke, HET0016 may also be injected to the hemorrhage site directly to treat cerebral vascular diseases. For example, in SAH, HET0016 can be injected directly into CSF via the Cistema Magna or a cannula placed subdurally to treat CVS. Injecting HET0016 into CSF directly might be a preferred route of administration following head injury since shunts are often placed in the skull to drain off CSF to reduce elevated cerebrospinal fluid pressure. The dose of HET0016 required for effectively treating cerebral vascular diseases when HET0016 is directly injected to the hemorrhage site can be similarly determined using the method described below for 17-ODYA. The CSF volume is about 10 ml for human and about 0.3 ml for rats. Thus, about 30 times more HET0016 is needed in human than in rats for treating cerebral vascular diseases.

The $IC_{50}$ for inhibition of 20-HETE formation is 1 µM for 17-ODYA and 3 µM for DDMS. Zou A P et al., *J Pharmacol Exp Therap* 268: 474-481, 1994; Alonso-Galicia, M. et al., *Hypertension* 29:320-325, 1997. Since 17-ODYA and DDMS cannot cross the blood-brain barrier, these drugs have to be introduced directly into CSF. Injecting 1.5 nmol of 17-ODYA into the Cisterna Magna of rats completely blocked the fall in cerebral blood flow following SAH. Assuming that CSF volume is 0.3 ml in rats, injecting 1.5 mmol of 17-ODYA into CSF would yield a final 17-ODYA concentration of 10 µM in CSF.

When 20-HETE synthesizing enzyme inhibitors other than HET0016, 17-ODYA and DDMS are to be used for treating cerebral vascular diseases, the $IC_{50}$s and the doses required to reach effective inhibitory concentrations following various routes of administration can be readily determined using the methods described above for HET0016.

Besides the 20-HETE synthesizing enzyme inhibitors described above, monoclonal or polyclonal antibodies against 20-HETE synthesizing enzyme can also be used as enzyme inhibitors for the purpose of this invention. Generally, it has been shown that an antibody can block the function of a target protein when administered into the body of an animal. Dahly, A. J., *FASEB J.* 14:A133, 2000; Dahly, A. J., *J. Am. Soc. Nephrology* 11:332A, 2000. Thus, an antibody against 20-HETE synthesizing enzyme can be used to treat a cerebral vascular disease defined in the present invention. For example, about 0.01 mg to about 100 mg, preferably about 0.1 mg to about 10 mg, and most preferably about 0.2 mg to about 1.0 mg of humanized CYP4A or CYP4F antibodies can be administered via an intramuscular injection to block CVS associated with overproduction of 20-HETE by cerebral vessels. The half life of these antibodies in a human being can be as long as 2-3 weeks. Antibodies can also be administered directly into CSF to block 20-HETE production associated with blood elements in CSF (SAH) or conditions associated with local inflammation of the brain (infections, ischemia). The DNA and protein amino acid sequences of all known members of the CYP4A and CYP4F families are published and available to one of ordinary skill in the art. One of ordinary skill in the art knows how to make a monoclonal or a polyclonal antibody to an enzyme. For example, antibodies against CYP4A1 and CYP4A10 have been made and these antibodies have been shown to inhibit the enzyme activity of CYP4A1 and CYP4A10. Amet, Y. et al., *Biochem Pharmacol.* 54(8): 947-952, 1997; Amet, Y. et al., *Biochem. Pharmacol.* 53(6): 765-771, 1997; Amet, Y. et al., *Alcohol Clin. Exp. Res.* 22(2): 455-462, 1998. Some anti-20-HETE synthesizing enzyme antibodies are also commercially available. For example, anti-CYP4A1 can be purchased from Gentest Corp. (Woburn, Mass.).

So far, we have described methods to reduce 20-HETE synthesizing enzyme activity by using enzyme inhibitors. Another way of reducing 20-HETE synthesizing enzyme activity is to lower the enzyme level. Many strategies are available to accomplish this. For example, one can increase the degradation rate of an enzyme or inhibit the synthesis of an enzyme. The synthesis of an enzyme can be inhibited at transcriptional level or translational level.

One common method to block the synthesis of a protein such as an enzyme is to use an antisense oligonucleotide (DNA or RNA) having a sequence complementary to at least part of the mRNA sequence of the protein to block translation. The cDNA sequence of all known members of the CYP4A and CYP4F families are published and available to one of ordinary skill in the art. One of ordinary skill in the art knows how to make and use an antisense oligonucleotide to block the synthesis of these enzymes. For example, antisense method has been used to effectively reduce CYP4A expression in the kidney blood vessels of rats in vivo, and to lower blood pressure and vascular tone. Wang, M. H. et al., *Am J Physiol* 276L F246-F253, 1999; Wang, M. H. et al., *Am J Physiol* 280:R255-R261, 2001.

An example of the antisense method for the present invention is to use 20-25 mer antisense oligonucleotides directed against 5' end of CYP4A1 (rat), CYP4A2 (rat), CYP4A11 (human), CYP4F2 (human), or CYP4F3 (human) message with phosphorothioate derivatives on the last three base pairs on the 3' end and the 5' end to enhance the half life and stability of the oligonucleotides. A useful strategy is to design several oligonucleotides with a sequence that extends 2-5 basepairs beyond the 5' start site of transcription. An appropriate antisense sequence for CYP4A1 includes, among others, 5'-cagtgcagagacgctcatggt-3' (SEQ ID NO:1) for DNA and 5'-cagugcagagacgcucauggu-3' (SEQ ID NO:2) for RNA. An appropriate antisense sequence for CYP4A2 includes, among others, 5'-gctaaatacagagaaacccatggt-3' (SEQ ID NO:3) for DNA and 5'-gcuaaauacagagaaac-cauggu-3' (SEQ ID NO:4) for RNA.

An antisense oligonucleotide used for treating a cerebral vascular disease defined in this invention can be administered intravenously into an animal with the disease. The oligonucleotide can also be administered into the CSF. A carrier for an antisense oligonucleotide can be used. An example of a suitable carrier is cationic liposomes. For example, an oligonucleotide can be mixed with cationic liposomes prepared by mixing 1-alpha dioleylphatidylcelthanolamine with dimethldioctadecylammonium bromide in a ratio of 5:2 in 1 ml of chloroform. The solvent will be evaporated and the lipids resuspended by sonication in 10 ml of saline. An oligonucleotide suspended in cationic liposomes should cross the blood-brain barrier. However, if it does not, it can be administered directly into CSF.

The dose of an antisense oligonucleotide used in the present invention can be from about 0.1 µg/kg body weight to about 100 µg/kg body weight, about 1 µg/kg body weight to about 10 µg/kg body weight, or about 3 µg/kg body weight to about 5 µg/kg body weight. Doses outside the above range but block synthesis of a target enzyme can also be used in the present invention.

Another way to use an antisense oligonucleotide is to engineer it into a vector so that the vector can produce an antisense cRNA that blocks the translation of the mRNAs encoding for the CYP4A or CYP4F enzymes that produce 20 HETE.

EXAMPLE 1

Treating Acute Fall in Blood Flow after SAH

Materials and Methods

Animals. Experiments were performed on male Sprague-Dawley rats (9-12 weeks old), purchased from Harlan Sprague-Dawley, Inc. (Indianapolis, Ind.). The rats were housed in an Animal Care Facility at the Medical College of Wisconsin, which is approved by the American Association for the Accreditation of Laboratory Animal Care. All protocols involving animals received approval by the Animal Care Committee of the Medical College of Wisconsin.

Surgical preparation. Rats were anesthetized with ketamine (Ketaject® 20 mg/kg i.m.) and thiobutabarbital sodium (Inactin® 50 mg/kg i.p.). A cannula was placed in the trachea and the rats were artificially ventilated using a small animal ventilator (SAR-830, CWE, Inc., Ardmore, Pa.) with a mixture of 30% $O_2$ in $N_2$. The femoral vein was cannulated for the infusion of drug and the rats received an i.v. infusion of 0.9% NaCl solution at a rate of 3 ml/min to replace fluid losses. The femoral artery was cannulated for measurement of mean arterial pressure (MAP) and arterial blood gases. Endtidal partial pressure of carbon dioxide ($pCO_2$) was controlled at 38 mmHg by adjusting the minute ventilation according to the reading of an $CO_2$ analyzer (Capstar-100 IITC, Inc., Woodland Hills, Calif.). Blood samples were collected at the beginning and end of the experiment and analyzed using a blood gas analyzer (ABL 300, Radiometer, Copenhagen, Denmark) to validate the endtidal $pCO_2$ readings. Anesthesia was maintained by administering additional amounts of thiobutabarbital (8 mg/kg i.v.) as needed. Rectal body temperature was maintained at 37±1° C.

Induction of SAH and measurement of cerebral blood flow. SAH was induced by injection of 0.3 ml autologous arterial blood into the Cisterna Magna using a modification of a posterior cranio-cervical approach of a model of SAH. Delgado T J et al., *Stroke* 16: 595-602 (1985); Solomon R A et al., *Stroke* 16: 58-64 (1985). The head of the rat was placed in a stereotactic head holder and the atlanto-occipital membrane was exposed by bluntly separating the overlying neck muscles in the midline. The occipital bone and the atlas were visualized. A 30 gauge needle attached to PE-10 was inserted using a stereomicroscope into the Cistema Magna by penetrating the atlanto-occipital membrane. Then, 0.3 ml of freshly drawn unheparinized arterial blood was injected into the Cistema Magna at a rate of 35 µl/min using a syringe pump. This created a massive SAH that was confirmed in all rats at autopsy. Blood was found overlying the cerebellomedullary junction posteriorly and around the basal artery and the vessels of the Circle of Willis.

Cerebral blood flow (CBF) was continuously measured using laser Doppler flowmetry through a thinned cranial window. A 3×5 mm area of the bone overlying the right parietal cortex was thinned using a hand-held drill until only a thin translucent layer of cranial bone remained (thinned cranial window). A PF 103 laser Doppler flow (LDF) probe was positioned over the cranial window and CBF was monitored using a PF-3 laser Doppler flowmeter (Perimed, Stockholm, Sweden).

Experimental protocol for testing the effects of HET0016 and 17-ODYA on rCBF when given before SAH. After surgery and a 30 min equilibration period, vehicle or HET0016 (10 mg/kg) were given i.v., and CBF was measured during a 30 min control period. Other animals received 17-ODYA (1.5 nmol) or vehicle in a volume of 50 µl that was injected directly into the Cistema Magna using a micromanipulator and a 30 gauge needle. The CBF recorded over the last 5 minutes of the control period immediately before initiation of SAH served as the control value. A blood sample (0.3 ml) was then collected from the femoral artery and infused over a 10 min period into the Cistema Magna. CBF was recorded for 2 min intervals at 10, 20, 30, 60, 90 and 120 minutes after completion of the injection of the blood. The CBF data are expressed as percentage change from control.

Experimental protocol for testing the effects of HET0016 on rCBF when given after SAH has been established. 0.3 ml of blood was injected into the Cistema Magna of rats to induce SAH. Thirty minutes later, vehicle or HET0016 (1 mg/kg) was injected i.v. The average CBF over the last 5 minutes before the injection of blood served as the control value and CBF was recorded for 2 min intervals at 10, 30, 40, 70, 100 and 160 minutes after induction of SAH. The CBF data are expressed as percentage change from control.

Measurement of 20-HETE in CSF. At the end of each experiment, CSF was collected from the Cisterna Magna using a 1 ml syringe and a 30 gauge needle. CSF was also collected from additional sham operated rats that did not receive an injection of blood into the Cisterna Magna. 20-HETE concentration in CSF was measured using a new fluorescent HPLC assay that was recently described. Maier K G et al., *Am. J. Physiol Heart Circ. Physiol.* 279: H863-H871 (2000). Briefly, 50 ng of an internal standard 20-hydroxyeicosa-6(Z), 15(Z)-dienoic acid (WIT-002) was added to the CSF samples (50 µl). The samples were extracted with 1 mL of ethyl acetate, the extract was dried under argon and the lipid fraction was purified on a Sep-Pak Vac™ column (cat. no. WAT054955, Waters Corporation, Milford, Mass.). The lipid fraction was labeled with 20 µl of acetonitrile containing 36.4 mM 2-(2,3-napthalimino)-ethyltrifluoromethanesulfonate. N,N-diisopropylethylamine (10 µl) was added to catalyze the reaction. The sample was reacted for 30 min at room temperature. Excess dye was removed using a Sep-Pak Vac™ column and the samples were dried under argon and were resuspended in 100 µl of methanol and analyzed by reverse-phase HPLC using a 4.6×250 mm Symmetry C18 column (Waters Corporation, Milford, Mass.) and a fluorescence detector (model number L-7480, Hitachi, Naperville, Ill.). The amount of 20-HETE in a sample was determined by comparing the area of the 20-HETE peak to that of the internal standard.

Characterization of HET0016 as a selective inhibitor of the formation of 20-HETE. These experiments examined the effects of various concentrations of HET0016 on the metabolism of AA in renal microsomes which are a rich source of the CYP enzymes that metabolize AA to 20-HETE and EETs. The renal cortex of rats was homogenized in a 10 mmol/L potassium phosphate buffer (pH 7.7) containing 250 mmol/L sucrose, 1 mmol/L EDTA, and 10 mmol/L magnesium chloride. Microsomes were prepared by differential centrifugation as previously described. Ma, Y-H et al., *Am J Physiol Regulatory Integrative Camp Physiol.* 267: R579-R589 (1994). CYP4A enzyme activity was assayed by incubating renal cortical microsomes (0.5 mg protein) for 30 min at 37° C. with [$^{14}$C]-AA (0.1 µCi/ml, 42 µmol/L, Amersham Corp., Arlington Heights, Ill.) in 1 ml of a 0.1 mol/L potassium phosphate buffer (pH 7.4) and 1 mmol/L NADPH as previously described. Ma, Y-H et al., *Am J Physiol Regulatory Integrative Camp Physiol.* 267: R579-R589 (1994). The reactions were terminated by acidification to pH 3.5 using 0.1 mol/L formic acid and extracted with ethyl acetate. Metabolites were separated using a 25 cm×2 mm i.d. (Supelco Inc., Bellefonte, Pa.) C18-reverse phase HPLC column and a linear elution gradient ranging from acetonitrile:water: acetic acid (50/50/0.1) to acetonitrile: acetic acid (100/0.1) over a 40 min period. The radioactive products were monitored using a radioactive flow detector (Model 120, Radiomatic Instrument Co., Tampa, Fla.).

Measurement of HET0016 levels in plasma and brain. Rats were given an i.v. injection of HET0016 (10 mg/kg) in 10% lecithin. After a one hour equilibration period, the rats were anesthesized with pentobarbital and a blood sample was collected from the jugular vein. The rats were then sacrificed and the brain was removed, weighed and homogenized in 3 volumes of 0.9% NaCl solution using a Physcotron homogenizer (Nition-Ikakikai, Chiba, Japan). The concentration of HET0016 in a 100 µl aliquot of plasma or brain homogenate was determined by LC/MS with selective ion monitoring. The samples were mixed with 1 ml of acetonitrile, centrifuged and 20 µl of the clear supernatant was injected into the LC/MS. The samples were separated on a 200×4.6 mm Capcellpak UG 120 ODS column (Shiseido Corp., Tokyo, Japan) and eluted with acetonitrile: water (72/28). Peaks were monitored using a Sciex API 3000 mass spectrometer (Perkin Elmer Sciex, Ontario, Canada) tuned to detect the precursor to product transitions specific for each analyte.

Drugs and Chemicals. All chemicals were HPLC grade. The fluorescent probe, (2-(2,3-napthalimino)ethyl trifluoromethanesulfonate) was purchased from Molecular Probes (Eugene, Oreg.). 17-ODYA was purchased from Sigma (St Louis, Mo.). HET0016 and WIT-002 were synthesized by Taisho Pharmaceutical Co. Ltd. (Saitama, Japan).

Statistics. Values are expressed as mean±SEM. Significance of differences in mean values within and between groups was examined by a two-way ANOVA for repeated measures followed by the Duncan multiple range test. A P value <0.05 was considered to be significant.

Results

Figure 2:
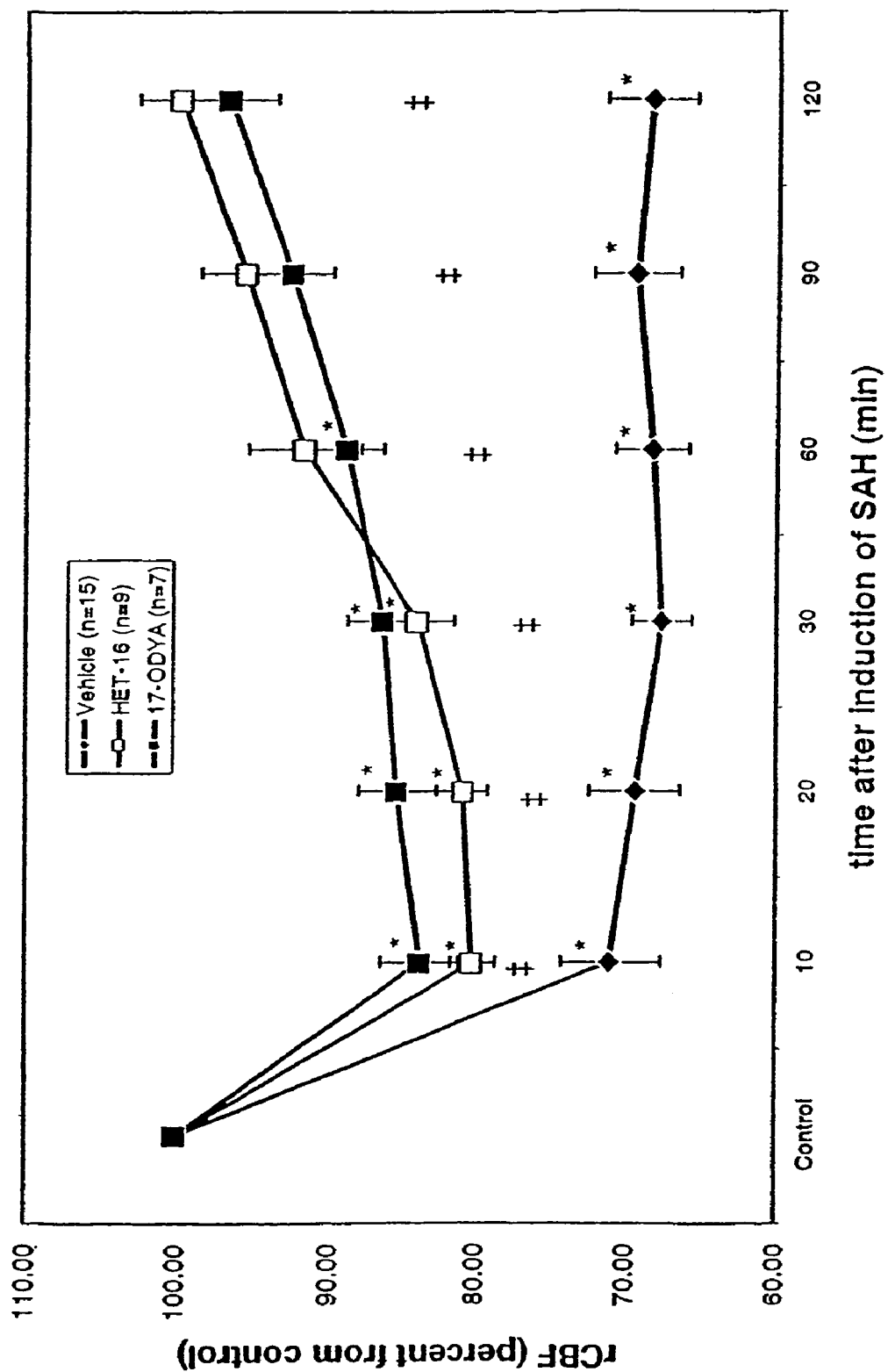
FIG. 2 shows the effect of HET0016 and 17-ODYA on regional cerebral blood flow (rCBF) after SAH when HET0016 and 17-ODYA were administered before the induction of SAH. * indicates significant differences from control. ‡ indicates significant differences from the corresponding value in vehicle treated groups.

Effects of HET0016 and 17-ODYA on rCBF when given before SAH. The effects of two chemically and mechanistically different inhibitors of the formation of 20-HETE on the changes in rCBF after induction of SAH are presented in FIG. 2. Rats were pretreated with HET0016 (10 mg/kg i.v., 30 min prior to SAH, n=9), 17-ODYA (1.5 nmol intrathecally, n=7) or vehicle (n=15). There was no significant difference in the response of rats that received the vehicle for HET0016 (lecithin) or 17-ODYA (1:1,000 ethanol in saline). Thus, the data from these two groups were combined and are presented together in FIG. 2. In vehicle treated rats, injection of 300 μl of blood into the Cisterna Magna caused a rapid decline in rCBF. It fell on the average 30%, 10 min after the induction of SAH and it remained at this level for the 2 hr course of the experiment. Pretreatment of the rats with the irreversible inhibitor of the formation of 20-HETE and EETs, 17-ODYA, or the novel selective inhibitor of the formation of 20-HETE, HET0016, markedly attenuated the fall in rCBF. Both drugs significantly reduced the initial fall in rCBF at 10 min by about 40% and rCBF recovered fully to values not significantly different from control within 60 minutes after induction of SAH in rats treated with HET0016 and within 90 minutes after induction of SAH in rats treated with 17-ODYA.

Physiological parameters. A comparison of the MAP and endtidal $pCO_2$ data in these experiments showed that there are no significant differences in endtidal $pCO_2$ at any time during the experiment in rats that received vehicle, HET0016, or 17-ODYA. MAP tended to decline during the experiment in all three groups but there is no difference in blood pressure in rats treated with vehicle, 17-ODYA or HET0016 at any time during the course of the experiment.

Figure 3:
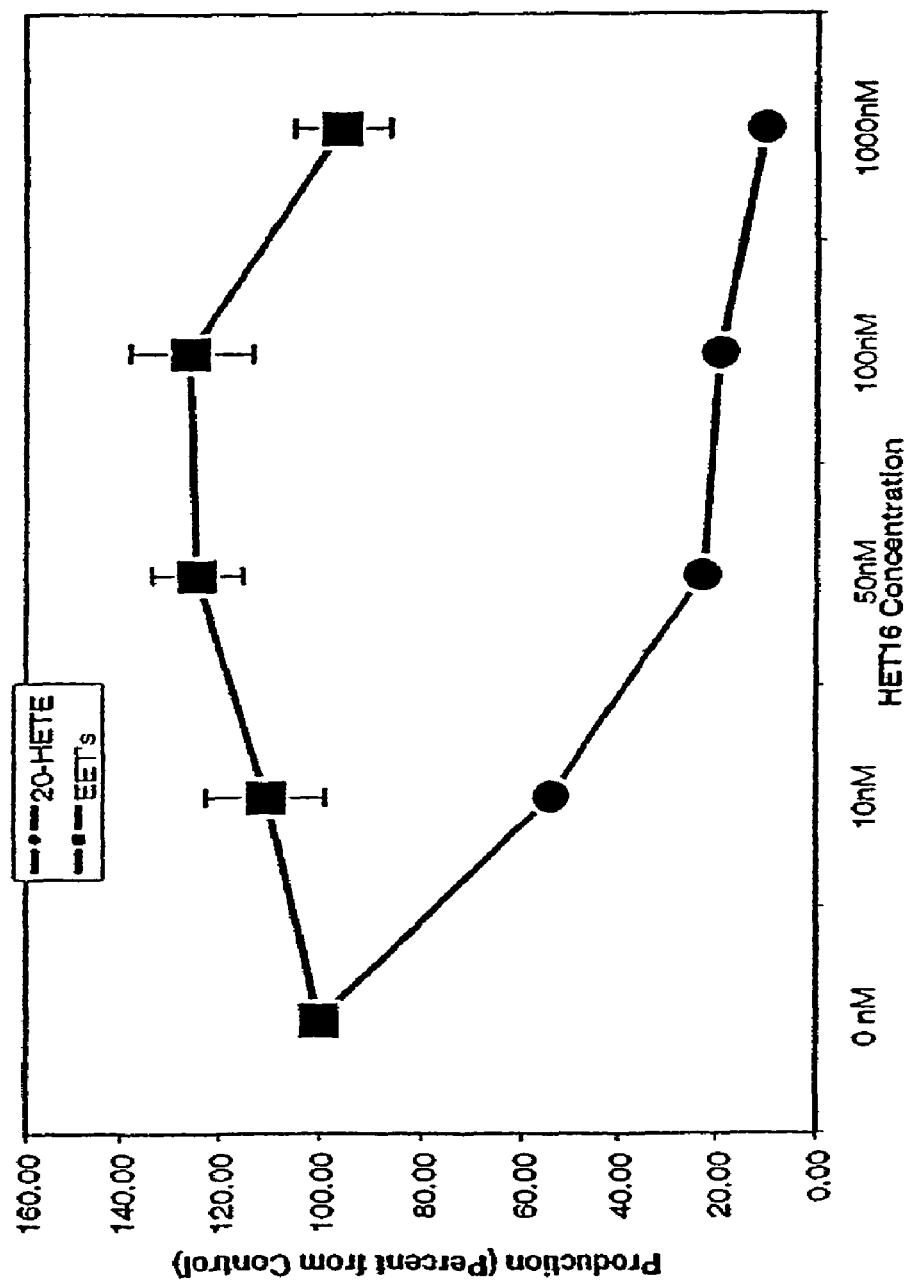
FIG. 3 shows the effect of HET0016 on the formation of 20-HETE and EETs in microsomes prepared from rat kidneys. * indicates significant differences from control. Error bars for 20-HETE are so small that they lie within the data points.

Effects on HET0016 on the synthesis of 20-HETE. Rat renal microsomes were used for these experiments because they express both CYP4A enzyme responsible for the formation of 20-HETE in cerebral arteries and enzymes of the CYP2C and CYP2J families that produce EETs. The effects of HET0016 on the metabolism of AA by rat renal microsomes are presented in FIG. 3. Mean values±SEM from 4 assays are presented. The data are expressed as a percentage of the control production of 20-HETE which averaged 96±3.9 pmoles/min per milligram protein. HET0016 inhibited the synthesis of 20-HETE in concentrations from 10-1,000 nmol/L in a dose-dependent manner. HET0016 had no significant effect on the production of EETs by renal microsomes even at a concentration as high as 1,000 nmol/L.

Measurement of HET0016 levels in plasma and brain. Levels of HET0016 averaged 570±90 ng/mL (n=3, 2.8 mmol/L) in the plasma and 1,488±104 ng/g (n=3, 7.2 μmol/L) in the brain 1 hr after i.v. injection of 10 mg/kg HET0016.

Figure 4:
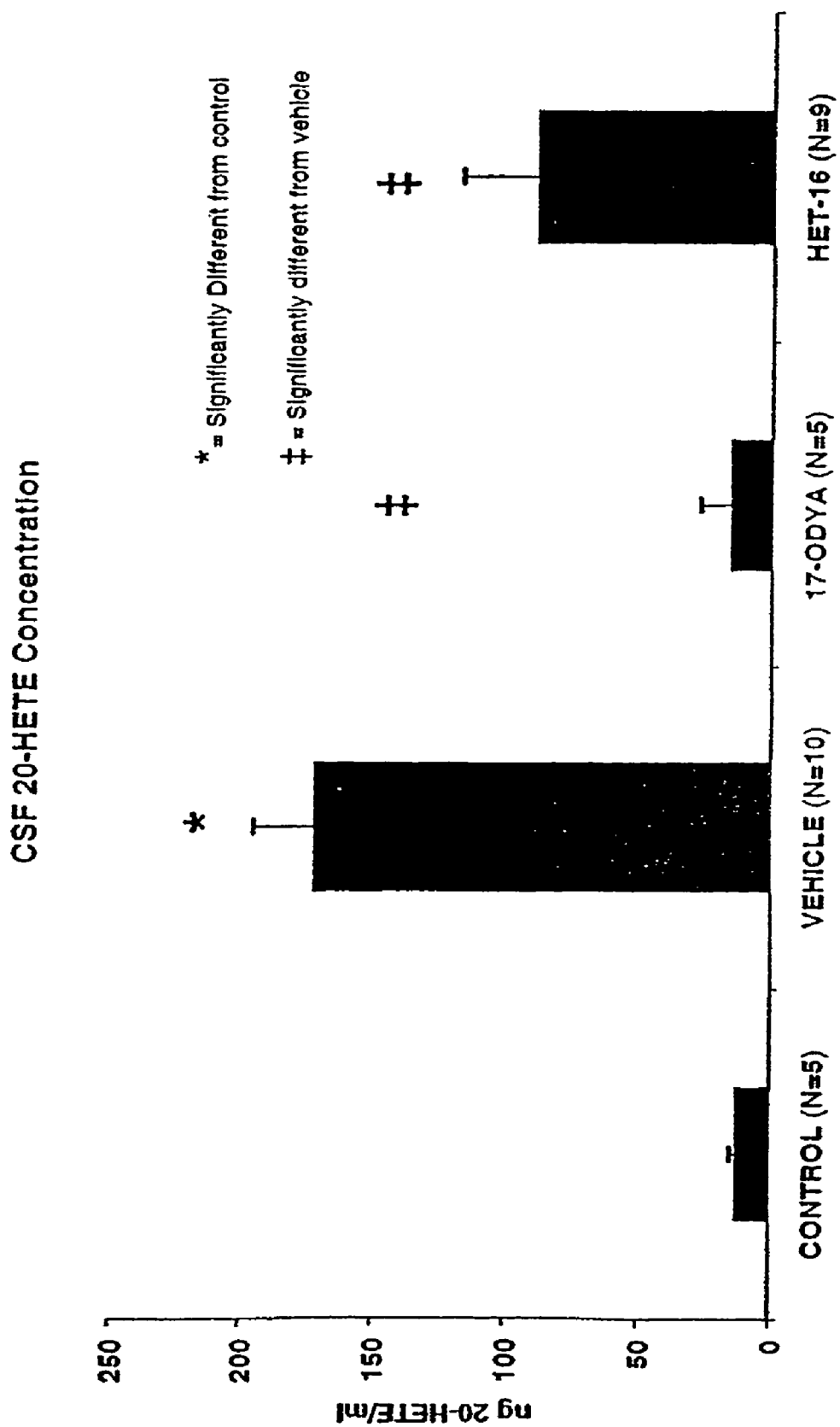
FIG. 4 depicts 20-HETE concentration in cerebrospinal fluid (CSF) before and after SAH and treatment of rats with 17-ODYA or HET0016. * indicates significant differences from control. ‡ indicates significant differences from vehicle treated groups.

Measurement of 20-HETE levels in CSF. Values for the concentration of 20-HETE in the CSF of sham operated control rats and 2 hr after SAH in rats given vehicle, 17-ODYA, and HET0016 are presented in FIG. 4. Numbers in parentheses indicate the number of animals studied. Rats that received vehicle had a 10-fold increase in the concentration of 20-HETE in CSF after SAH as compared to the levels measured in control rats that did not receive an injection of blood. Rats that received either 17-ODYA or HET0016 prior to the induction of SAH had a significantly lower concentration of 20-HETE in the CSF. The fall of 20-HETE levels in CSF was greater in rats that received 17-ODYA than that seen in rats treated with HET0016.

Figure 5:
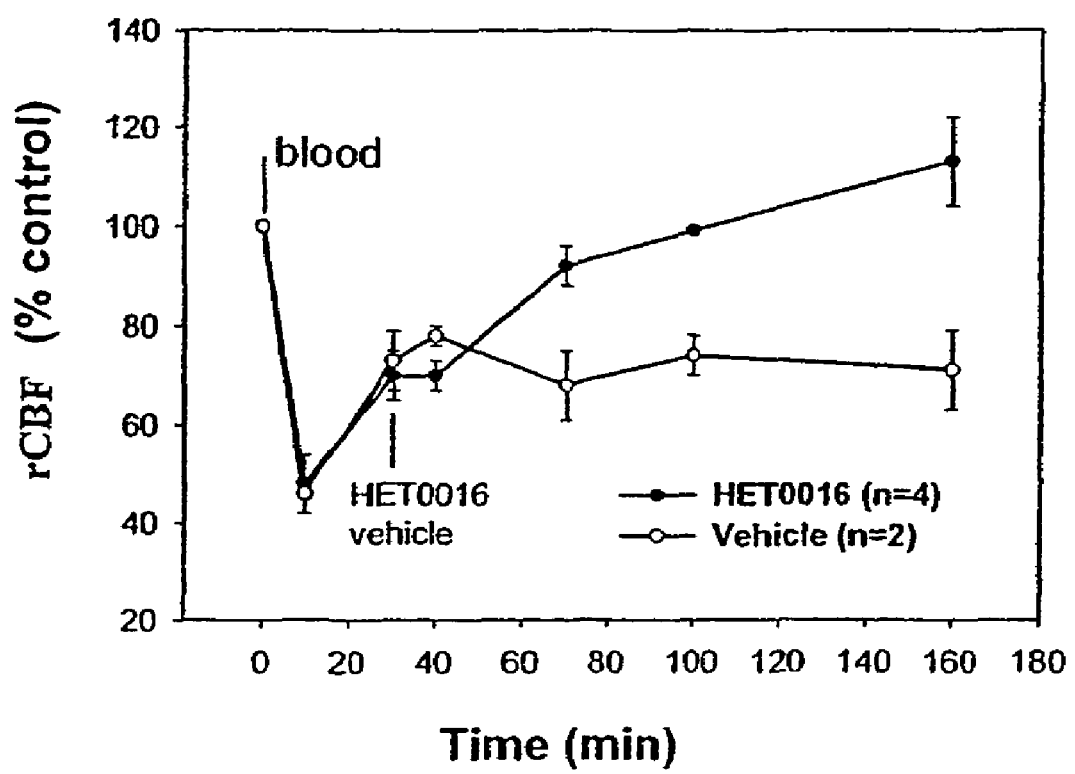
FIG. 5 shows the effect of HET0016 on rCBF after SAH when HET0016 was administered 30 minutes after SAH was initiated.

Ability of HET0016 to reverse the fall in cerebral blood flow when given after SAH is induced. 0.3 ml of blood was injected into the Cisterna Magna of rats to induce SAH. As shown in FIG. 5, the injection of blood lowered cerebral blood flow transiently by 60% followed by a sustained decrease of cerebral blood flow of 30%. Treating the rats with HET0016 (1 mg/kg body weight, i.v.) 30 min after the induction of SAH brought cerebral blood flow back to the control value 70 min later. In contrast, the cerebral blood flow in vehicle treated rats remained low through out the experiment period of 160 minutes. The data shown in FIG. 5 indicates that HET0016 is an effective therapeutic agent to treat and reverse the fall in cerebral blood flow and consequent brain damage following SAH.

EXAMPLE 2

Effect of HET0016 on Infarct Volume in Rats with Transient MCA Occlusion

Methods

Adult male Wistar rats (200-250 g) were anesthetized with 2% halothane in $O_2$ gas. The right external carotid artery (ECA) was carefully dissected. A silicon-coated suture (18 mm-long) was inserted from the lumen of the ECA to the right internal carotid artery (ICA) to occlude the origin of the right middle cerebral artery (MCA). Body temperature was maintained at 37° C. with a heating pad. After surgery, anesthesia was discontinued, and ischemic animal exhibited severe hemiparesis in the upper extremities. One hour after MCA occlusion, the thread was removed to allow reperfusion of the ischemic area. Rats were given vehicle (30% hydroxypropyl beta-cyclodextrin) or HET0016 (0.01, 0.1 and 1 mg/kg i.v.) just after reperfusion.

To measure infarct volume, rats were killed after 24 hours of reperfusion following transient occlusion of the MCA. Brains were flushed transcardially with physiological saline, removed from the skull, and cut into 2-mm coronal sections. The slices were immersed in 2% triphenyltetrazolium chloride (TTC) solution at 37° C. for 30 minutes.

All values were presented as mean±SEM. For statistical analysis, Dunnett's multiple-range test was used.

Results

Figure 6:
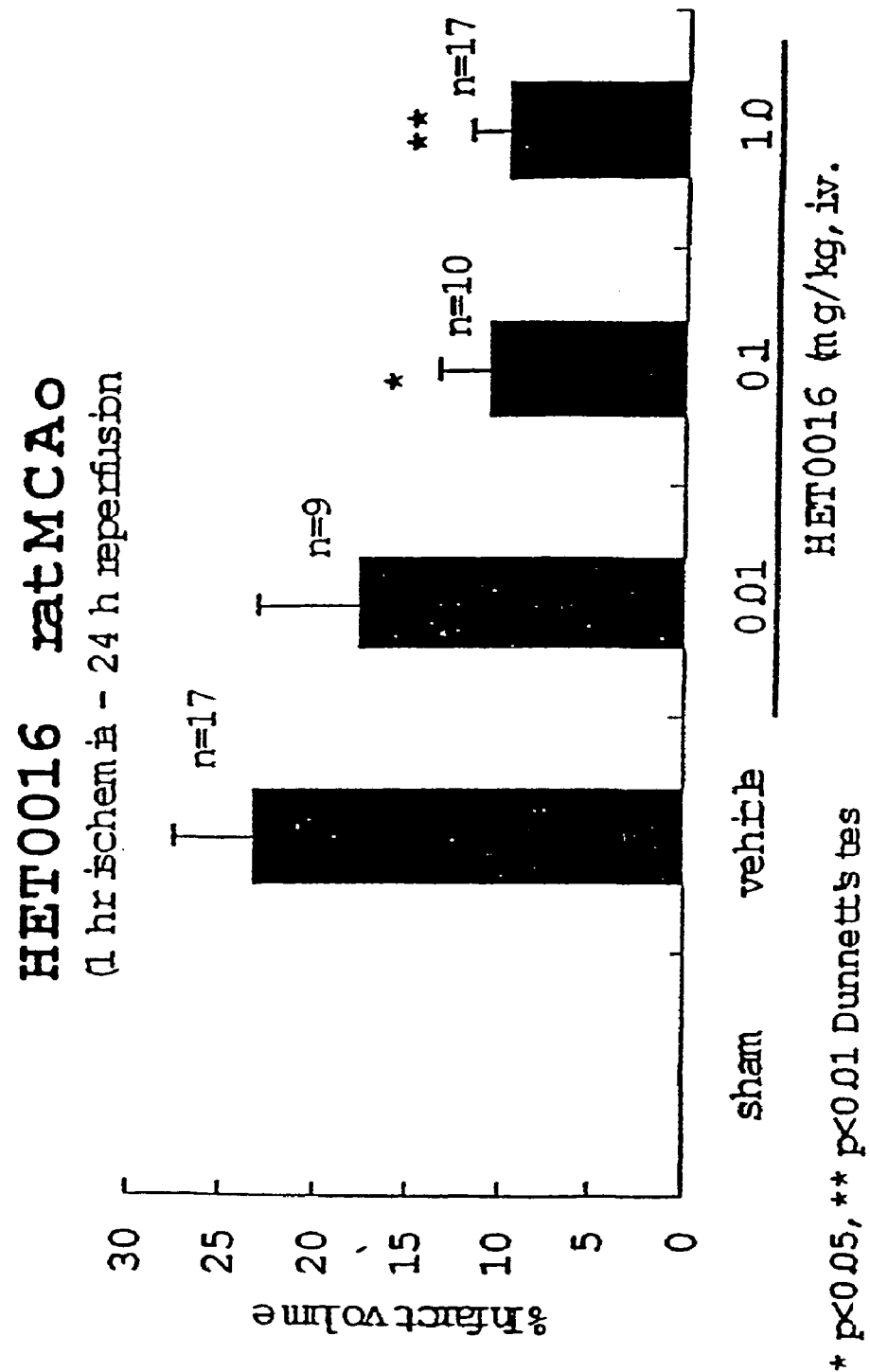
FIG. 6 shows the effect of HET0016 on the infarct volume following the transient occlusion of the middle cerebral artery of rats.

Intravenous injections of HET0016 significantly decreased the infarct volume in rats with MCA occlusion at the dose of 0.1 and 1 mg/kg (FIG. 6). The infarct volume (%) in vehicle group, 0.1 mg/kg HET0016 group, and 1 mg/kg HET0016 group were 23.3±4.1% (n=17), 10.7±2.6% (n=10, $p<0.05$), and 9.7±2.1% (n=17, $p<0.05$).

EXAMPLE 3

20-HETE/EET Selectivity of 20-HETE Synthesizing Enzyme Inhibitors

Methods

All procedure was carried out at 4° C. Renal cortex was pooled from twenty male SHR rats (6 weeks of age). They were homogenized extensively in lysis buffer (20 mM HEPES, pH 7.4, 1 mM EDTA, 100 μM p-(amidinophenyl) metanesulfonyl fluoride and 250 mM sucrose), and centrifuged at 16,000×g for 10 min. Supernatant was further centrifuged at 16,000×g for 30 min. Soluble fraction was collected and centrifuged at 200,000×g for 30 min. The resulting pellet was suspended in 50 mM MOPS buffer.

Microsomes were incubated in 50 mM MOPS buffer with [$^3$H]-AA (1 μCi/ml) in the presence or absence of HET0016, 1-ABT, or miconazole. β-NADPH (1 mM) was added to the reaction mixture and the reaction mixture was further incubated for 1.5 hr at 37° C. The reaction was terminated by adding formic acid and acetonitrile to a final concentration of 1% and 50%, respectively. Aliquots of mixture were applied to a Bio-Sil C18HL90-5S column (150×4.6 mm) and then 20-HETE was eluted at a flow rate of 0.7 ml/min with a gradient of solvent A (100% acetonitrile) and B (0.1% acetic acid) as described below: 0-10 min, 48% of A to 64.8% of A; 10-25 min, 64.8% of A to 75% of A; 25-26 min 75% of A.

Results

Figure 7:
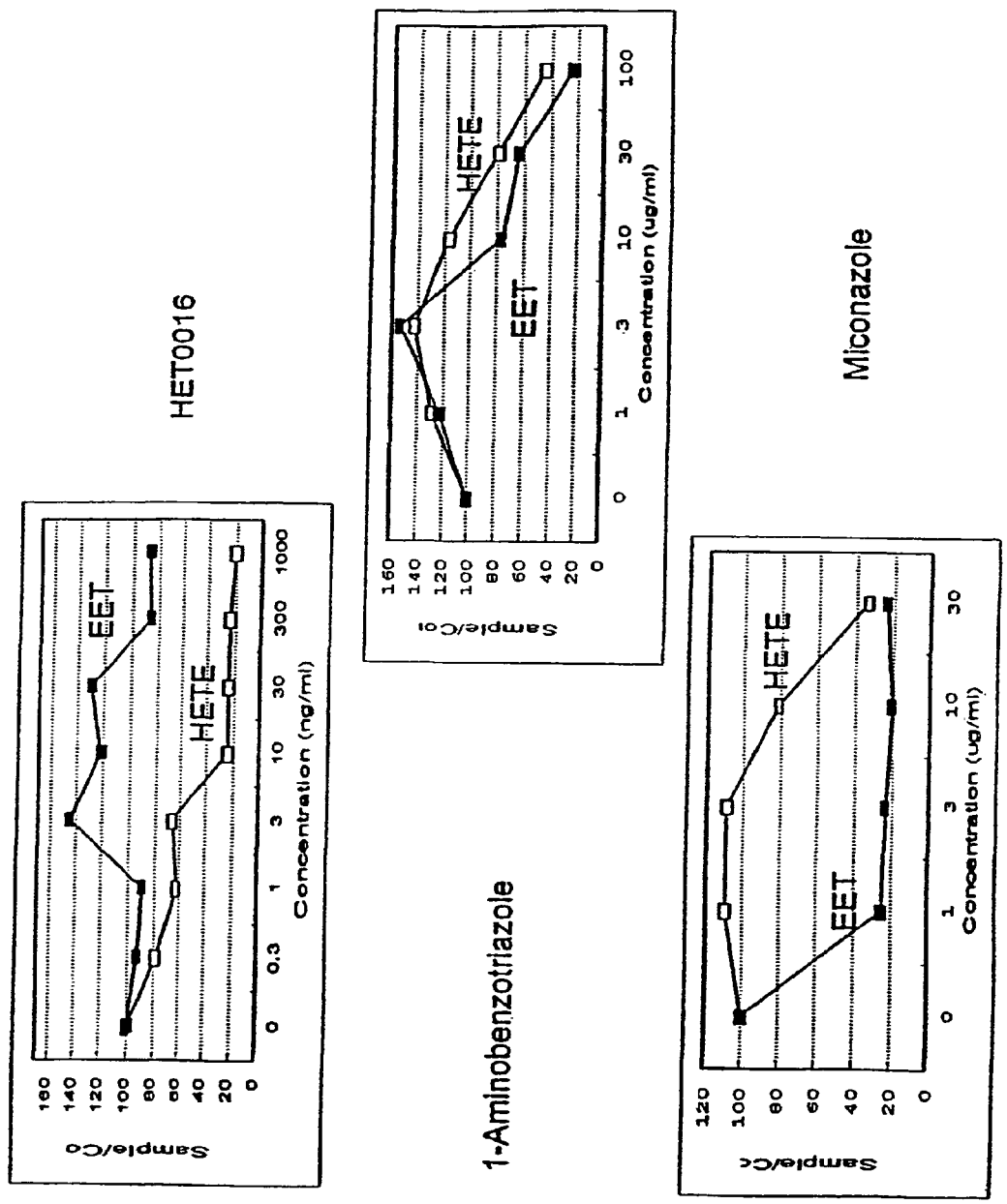
FIG. 7 compares the effect of HET0016, 1-aminobenzotriazole (1-ABT), and miconazole on 20-HETE synthesis and EET synthesis in microsomes prepared from rat kidneys.

As shown in FIG. 7, HET0016 (MW=206) potently inhibited the 20-HETE formation in a dose-dependent manner. The $IC_{50}$ in this experiment averaged 4 ng/ml which corresponds to a molar concentration of 20 nM. However, HET0016 did not inhibit the EET formation in rat renal microsomes even at the highest concentration studied (1,000 ng/ml, or 5 µM). 1-ABT (MW=134) is a nonselective inhibitor that reduced the formation of both EETs and 20-HETE in a dose-dependent manner. The $IC_{50}$ for 1-ABT is approximately 20 µg/ml, or 150 µM. Miconazole (MW=479) is a selective inhibitor of the formation of EETs with an $IC_{50}$ of approximately 0.5 µg/ml, or 1 µM. Only at very high concentrations (10-20 µg/ml, 21-42 µM) did miconazole inhibit the formation of 20-HETE. These results suggest that among these CYP450 inhibitors, HET0016 is a 20-HETE selective CYP450 inhibitor in rat renal microsomes. It is also at least 1,000 times more potent than other compounds.

EXAMPLE 4

20-HETE Producing Activity in Canine Neutrophils

Methods

Experiments were performed to determine the cell type in canine blood responsible for the formation of 20-HETE. Experiments were performed using 4 male Beagle dogs. The dogs were anesthetized with sodium pentobarbital (30 mg/kg, i.v.). Venous blood sample was drawn and immediately mixed with 1:9 volume of trisodium citrate (3.8%) as an anticoagulant. Neutrophils were prepared to 98% purity using a percoll gradient technique. CSF was drawn from the Cisterna Magna by using a 20 gauge needle. Only clear CSF sample without blood was used for the present experiment. The CSF was oxygenated with mixed gas (95% $O_2$, 5% $CO_2$) for 30 min. Neutrophils were suspended in the oxygenated CSF and cell numbers were adjusted to $2\times10^6$, $6.3\times10^6$, and $2\times10^7$. Whole blood (20 µl), red blood cells (20 µl) or neutrophils were incubated in the oxygenated CSF (180 µl) including 1 mM NADPH and [$^3$H]-AA at 37° C. for 2 hrs. The reaction was terminated by the addition of formic acid. One hundred percent acetonitrile (200 µl) was added to the reaction buffer to adjust final concentration to 50% for HPLC separation. Metabolites of AA were separated on a Bio-sil C18HL90-5S column (150×4.6 mm) at a flow rate of 0.7 ml/min using a gradient elution ranging from acetonitrile:water:acetic acid (48/52/0.1) to acetonitrile:water:acetic acid (75/25/0.1) over a 26 min period. The labeled products formed were monitored using a radioactive flow detector (raytest GmbH, Straubenhardt, Germany).

Results

Figure 8:
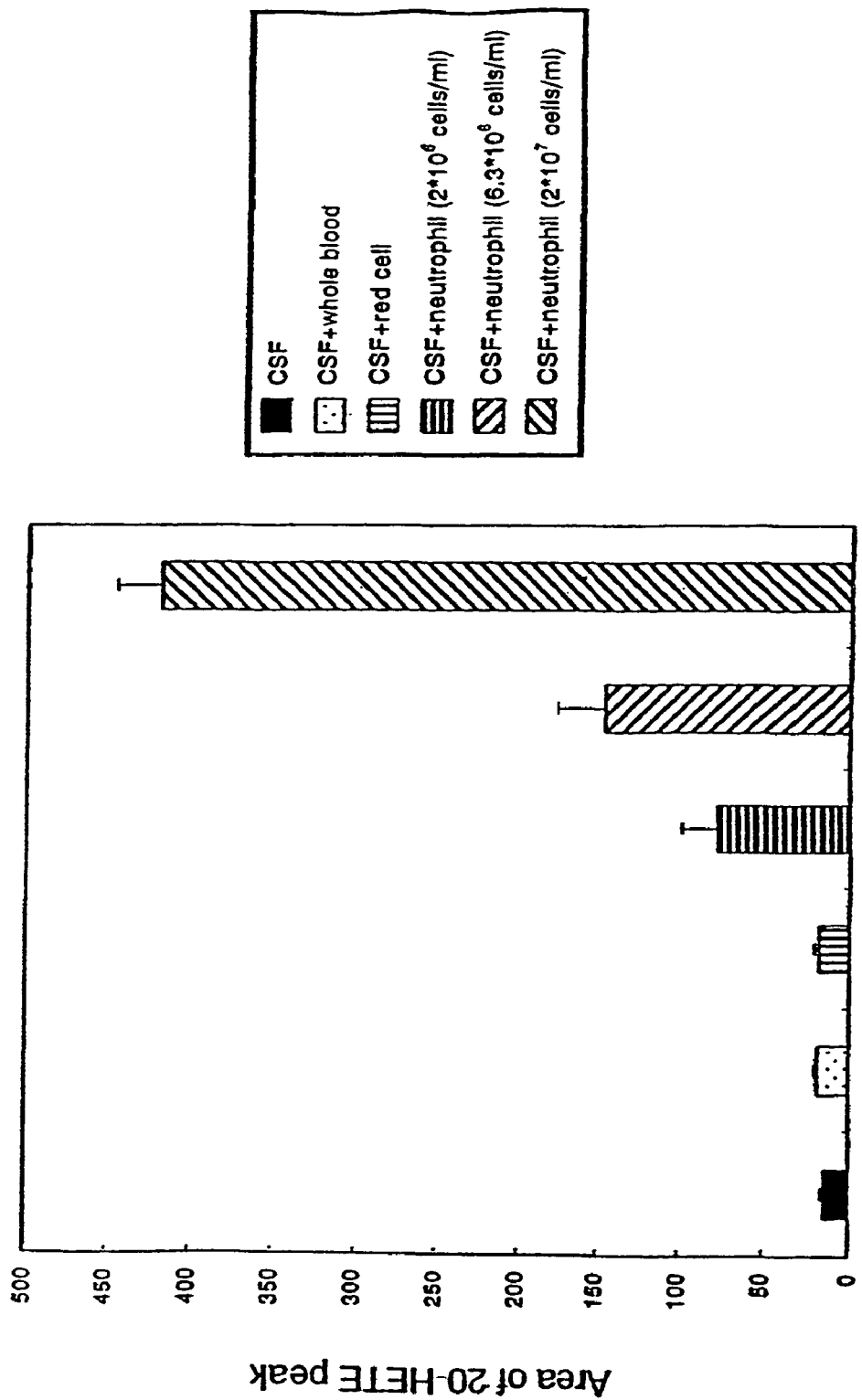
FIG. 8 shows the ability of canine PMNs to produce 20-HETE.

Results from this experiment show that neutrophils in canine blood produced 20-HETE (FIG. 8). We have obtained similar data using rat neutrophils.

EXAMPLE 5

Effects of HET0016 on 20-HETE Producing Activity in Canine Neutrophils

Methods

We next examined the ability of various concentrations of HET0016 to inhibit the formation of 20-HETE by canine neutrophils. Canine neutrophils ($2\times10^7$ cells at a final concentration) were incubated in dog CSF in the presence of 1 mM NADPH and [$^3$H]-AA at 37° C. for 2 hours in the absence or presence of various concentrations of HET0016 ($10^{-11}$, $10^{-10}$, $10^{-9}$, $10^{-8}$, $10^{-7}$, and $10^{-6}$ M). The reactions were terminated by addition of formic acid. Acetonitrile was added to the reaction buffer to adjust final concentration to 50% for HPLC separation. Metabolites of AA were separated on a Bio-sil C18HL90-5S column (150×4.6 mm) at a flow rate of 0.7 ml/min using a gradient elusion ranging from acetonitrile:water:acetic acid (48/52/0.1) to acetonitrile:water:acetic acid (75/25/0.1) over a 26 min period. The labeled metabolites were monitored using a radioactive flow detector ramona 93 (raytest GmbH, Straubenhardt, Germany).

Results

Figure 9:
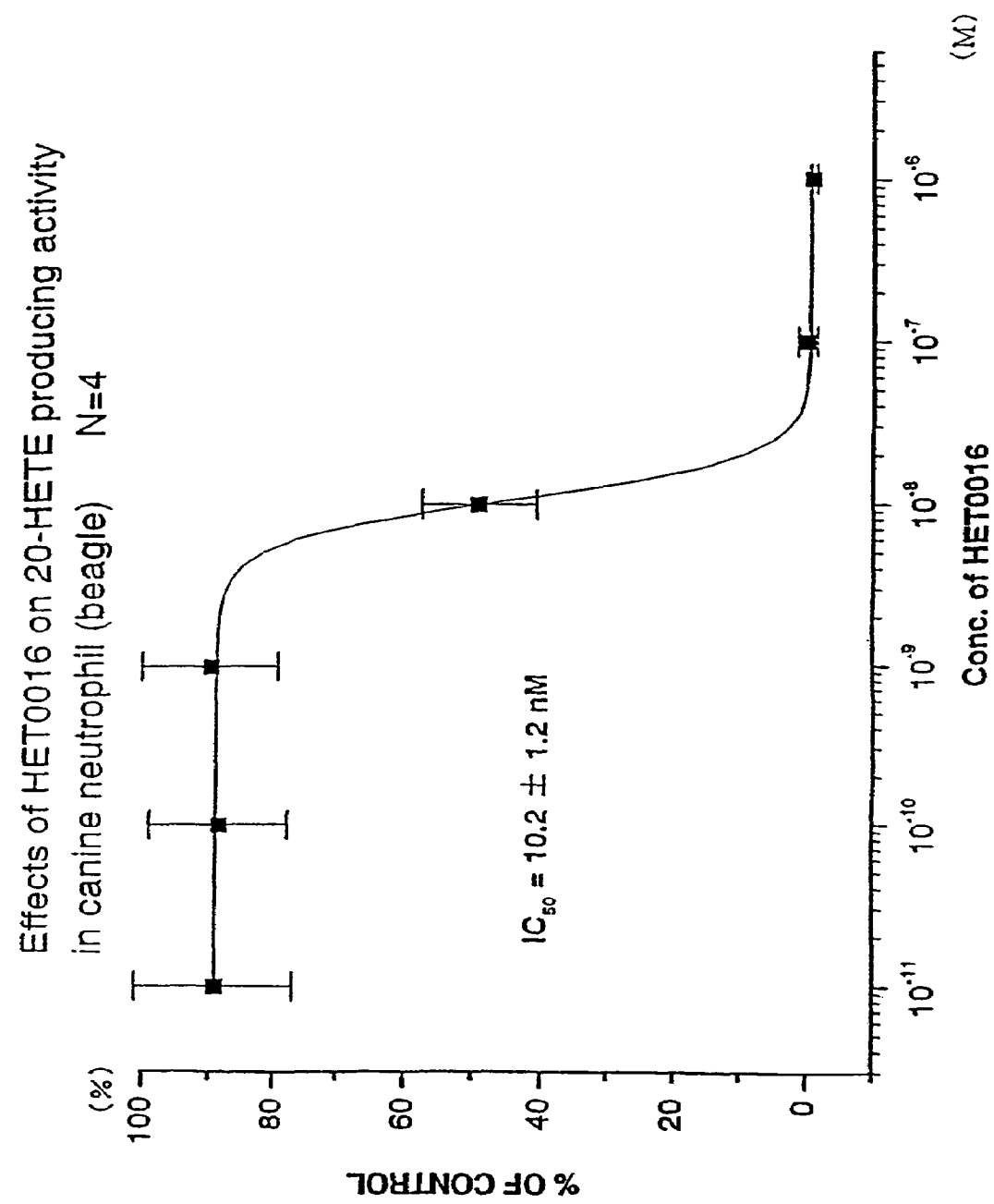
FIG. 9 shows the effect of HET0016 on the synthesis of 20-HETE by canine neutrophils.

HET0016 ($10^{-11}$-$10^{-6}$ M) inhibited the formation of 20-HETE by canine neutrophils in a concentration-dependent manner (FIG. 9). The $IC_{50}$ for HET0016 averaged 10.2±1.3 nM (n=4).

EXAMPLE 6

Measurement of 20-HETE Levels of CSF in Dogs with SAH

Methods

Male beagle dogs were used in the present study. The double-hemorrhage canine model was employed since it allows reliable reproduction of chronic vasospasm.

On Day 1, surgical manipulation was performed under anesthesia. SAH was induced by inserting a 20 gauge needle into the Cisterna Magna, and 2 to 6 ml of CSF was removed. Fresh autologous arterial blood (5 to 10 ml) was injected into the Cisterna Magna. The dogs were then tilted with the tail up for 20 min to facilitate setting of the blood around the basilar artery by gravity. Then, the animals were permitted to awaken and were returned to individual cages. On Day 3, the dogs were anesthetized and 0.5 ml to 4 ml of CSF was withdrawn, and 5.5 to 9 ml of fresh autologous arterial blood was injected into the Cisterna Magna, as described for Day 1. The animals were then returned to their cages. On Day 7, the CSF sample (0.5 ml to 2 ml) was withdrawn by the same operation. 20-HETE levels in CSF were measured by the HPLC technique as described by Maier, K. G. et al., *Am. J. Physiol Heart Circ. Physiol.* 279: H863-H871 (2000).

Results

Figure 10:
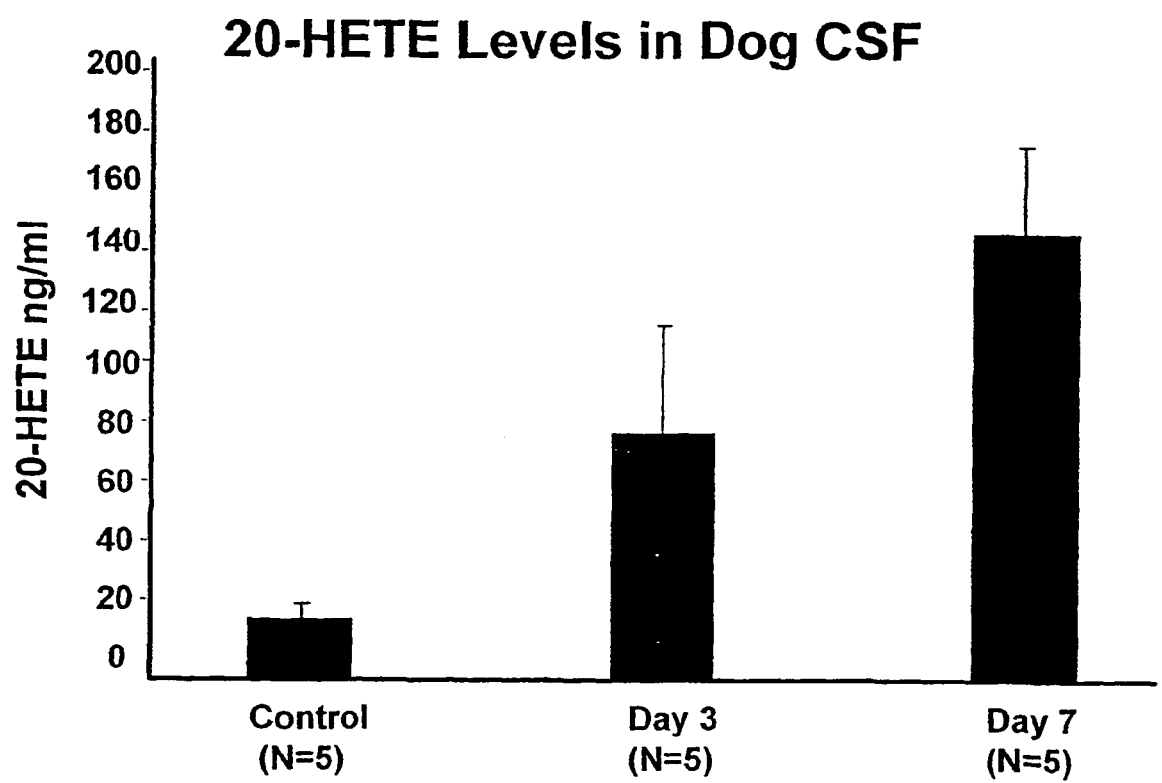
FIG. 10 shows the effects of SAH on levels of 20-HETE in CSF of Dogs.

20-HETE levels of CSF in the control period was 20.2±4.7 ng/ml (n=5). We found that injection of blood into the Cisterna Magna increased the 20-HETE levels in the CSF of dogs with SAH (FIG. 10). The levels of 20-HETE in CSF at Day 3 and Day 7 were 81.6±29.6 ng/ml (n=5) and 148.1±36.6 ng/ml (n=5) (FIG. 10).

EXAMPLE 7

Inhibition of Human 20-HETE Synthesizing Enzyme

Methods

Reaction mixtures containing HBSS (Hanks' Balanced Salt Solution, Catalog No. 14175, Gibco), 5 µCi/ml $^3$H-AA (Amersham Pharmacia Biotech), 1 mM NADPH, and human renal microsomes (Human Cell Culture Center, Laurel, Md.) (0.02-0.4 mg of protein) were incubated at 37° C. for 2 hrs. In the inhibition studies, HET0016, 17-ODYA, or 1-ABT was added directly to the reaction mixtures. All reactions were terminated by acidification with 1% formic acid. Equal volume of acetonitrile was added and finally 50% acetonitrile mixtures were subjected to HPLC analysis. Aliquots of reaction mixture were applied on a Bio-Sil C18 HL 90-5S column (150×4.6 mm, Bio-Rad) and reaction products were separated using a linear gradient with mixture of solvent A (100% acetonitrile) and solvent B (0.1% acetic acid) as follows: (i) 0-10 min, 48 to 64.8% of solvent A; (ii) 10-20 min, 64.8 to 75% of solvent A; (iii) 25-26 min, 75% of solvent A; (iv) 26-31 min, 100% of solvent A. $^3$H-labeled products were detected using a radioactive detector (raytest, ramina 93). 20-HETE had a retention time of about 16 min in our system (HPLC, Gilson System, 805 (manometoric module), 811C (Dynamic mixer), 401C (diluter), 305 (pump), 306 (pump), 231XL (sampling injector), 831 (temperature regulator), 503 (degasser)). $IC_{50}$ was defined as the concentration of inhibitor by which the peak area of 20-HETE was reduced to 50% of control.

Results

HET0016 ($10^{-11}$-$10^{-6}$ M), 17-ODYA ($10^{-9}$-$10^{-4}$ M) and 1-ABT ($10^{-9}$-$10^{-4}$ M) inhibited the formation of 20-HETE by human renal microsomes incubated with AA in a concentration-dependent manner. The $IC_{50}$ values for HET0016, 17-ODYA, and 1-ABT were 8.9±2.7 nM (n=6), 1.8±0.8 µM (n=6), and 38.5±14.9 µM (n=5), respectively.

EXAMPLE 8

Effects of HET0016 on All the CYP Isoforms, CYP4A11, CYP4F2 and CYP4F3 Responsible for the Formation of 20-HETE in Humans Methods Thirty pmoles of recombinant CYP4A11, CYP4F2 or CYP4F3 enzymes purchased from Gentest Corp. (Woburn, Mass.) were incubated at 37° C. for 30 min with [$^{14}$C]-AA (0.1 Ci, 1.9 M) in 1 ml of a 0.1 M potassium phosphate buffer (pH 7.4) containing 1 mM NADPH. The reactions were terminated by acidification to pH 3.5 with formic acid and extracted with ethyl acetate. Metabolites were separated by reverse phase HPLC and products were monitored using a radioactive flow detector.

Results

Representative chromatograms obtained with CYP4F3 are presented in FIG. 11, panels A (control) and B (1 µM HET0016). Similar results were obtained using CYP4A11 or CYPF2 enzymes. All three isoforms produced 20-HETE when incubated with AA. CYP4F3 isoform had the greatest activity, followed by CYP4F2 and CYP4A11. HET0016 inhibited the formation of 20-HETE by all three isoforms in a concentration dependent manner (FIG. 11, panel C). The $IC_{50}$ for CYP4A11 was 42 nM and it averaged 100 nM and 125 nM for the CYP4F3 and CYP4F2 isoforms, respectively.

EXAMPLE 9

Effects of HET0016, 17-ODYA and 1-ABT on the Activity of the Major Human Hepatic CYP Enzymes, CYP2D6, 2C9 and 3A4, Involved in Drug Metabolism Methods HET0016, 17-ODYA, and 1-ABT were tested for their ability to inhibit the catalytic activity of common human liver cytochrome P450 enzymes (CYP2D6, 2C9 and 3A4) involved in drug metabolism. Microsomes prepared from the livers of 15 humans was purchased from Nippon Nosanko. The enzyme/substrate contained buffer, human liver microsomes and the following substrates (CYP2C9: $^{14}$C-tolubutamide (4-methylhydroxylation), CYP2D6: bufuralol hydrochloride (1'-hydroxylation), CYP3A4: $^{14}$C-testosterone, and CYP2C19: $^{14}$C-(S)-mephenyloin (4'-hydroxylation). Above-mentioned mixture was incubated with or without 1-ABT (100 µM), 17-ODYA (10 µM), or various concentrations of HET0016 (1, 10, 100 µM). After the incubation, the rate of formation of the oxidized substrates (metabolites) were determined using TLC or HPLC. Positive controls for CYP2C9, CYP2D6, CYP3A4 and CYP2C19 were sulfaphenazol, quinidine, ketoconazole and tranylcypromaine.

Effects of HET0016 on COX activity. The effect of HET0016 on COX activity was examined using the COX inhibitor screening assay kit (Cayman Chemical Co., Ann Arbor, Mich.). In brief, the purified enzyme from ram seminal vesicles PGH1 synthase was incubated with 100 µM of AA in 1.0 ml of incubation buffer (0.1 M Tris-HCl, pH 8, 5 mM EDTA, 2 mM phenol and 1 µM hematin) with or without HET0016 ($10^{-10}$-$10^{-4}$ M) and indomethacin ($10^{-10}$-$10^{-4}$ M). Reaction mixtures were incubated at 37° C. for 2 min before the addition of AA and for 2 min thereafter. All samples were run in duplicate. Amounts of $PGE_2$ were determined by EIA after 100-400 times dilution with Tris buffer.

Results

Table 1 shows the inhibitory effects of HET0016, 17-ODYA and 1-ABT on human CYP2C9, CYP2C19, CYP2D6 and CYP3A4 activity. The corresponding positive controls inhibited the metabolism of CYP2C9, 2D6 and 3A4 by approximately 90%, and CYP2C19 activity by 65%. 1-ABT at a concentration of 100 µM inhibited the activity of these CYP isoforms by 40-80%. 17-ODYA, at a concentration of 10 µM which could substantially inhibit CYP4A activity, was more selective than 1-ABT and only reduced CYP 2C9 and CYP3A4 activity by 20-30%. Similarly, HET0016 at a concentration of 1 µM, that is 100 fold greater than the concentration needed to inhibit the formation of 20-HETE, only reduced the activity of CYP2C19 and CYP3A4 by 27%. At higher concentrations of 10 µM and 100 µM, HET0016 reduced the activity of the CYP isoforms more substantially. However, 10 µM and 100 µM exceed the effective concentration of HET0016 needed for inhibition of 20-HETE formation by 1,000 and 10,000 times, respectively.

We also examined the effects of HET0016 on COX activity by measuring the PGH1 synthase-catalyzed conversion of AA to $PGE_2$. HET0016 ($10^{-6}$ M) inhibited the COX activity by 20%, while indomethacin ($10^{-6}$ M) inhibited the COX activity by 95%.

TABLE 1

Effects of HET0016, 17-ODYA and 1-ABT on CYP specific activities catalyzed by human liver microsomes

| Drugs | Inhibitor Concentration (µM) | % Inhibition (duplicate) | | | |
|---|---|---|---|---|---|
| | | CYP2C9 | CYP2C19 | CYP2D6 | CYP3A4 |
| Positive control | — | 91 | 64 | 91 | 89 |
| 1-ABT | 100 | 66 | 75 | 42 | 81 |

TABLE 1-continued

Effects of HET0016, 17-ODYA and 1-ABT on CYP specific activities catalyzed by human liver microsomes

| Drugs | Inhibitor Concentration (µM) | % Inhibition (duplicate) | | | |
|---|---|---|---|---|---|
| | | CYP2C9 | CYP2C19 | CYP2D6 | CYP3A4 |
| 17-ODYA | 10 | 23 | 10 | −3 | 29 |
| HET0016 | 1 | 9 | 27 | 8 | 27 |
| | 10 | 68 | 94 | 48 | 67 |
| | 100 | 95 | 100 | 77 | 82 |

Positive control:
2C9: sulfaphenazol,
2C19: Tranylcypromine,
2D6: Quinidine,
3A4: Ketoconazole.
Human liver microsome: pooled microsome from 15 donors.

We claim:

1. A method for treating a cerebral vascular disease in a human or non-human animal wherein the cerebral vascular disease is selected from occlusive stroke, hemorrhagic stroke, cerebrovasospasm associated with hemorrhagic stroke, and accumulation of blood in subarachnoid space caused by head injury, the method comprising the step of:

administering N-hydroxy-N-(4-butyl-2-methylphenyl)-formamidine (HET0016) into a human or non-human animal having said disease in an amount sufficient to increase or prevent a decrease in cerebral blood flow in the human or non-human animal.

2. The method of claim 1, wherein HET0016 is administered at a dose sufficient to achieve a blood concentration of about 1 nM to about 1,000 nM.

3. The method of claim 1, wherein HET0016 is administered at a dose sufficient to achieve a blood concentration of about 2 nM to about 25 nM.

4. The method of claim 1, wherein HET0016 is administered intravenously.

5. The method of claim 4, wherein HET0016 is administered at a dose between about 0.003 mg/kg body weight and about 10 mg/kg body weight.

* * * * *